United States Patent [19]

Boland

[11] Patent Number: 4,576,158

[45] Date of Patent: Mar. 18, 1986

[54] METHOD FOR DETERMINING THE STABILITY OF AN ORTHOPEDIC DEVICE COMPOSED OF AN EXTERNAL FIXATION BAR DURING SETTING OF BONE FRACTURES

[75] Inventor: Michel A. G. Boland, Ham-sur-Heure, Belgium

[73] Assignee: Region Wallone, Brussels, Belgium

[21] Appl. No.: 569,558

[22] Filed: Jan. 10, 1984

[30] Foreign Application Priority Data

Jan. 28, 1983 [BE] Belgium ............................... 895728

[51] Int. Cl.$^4$ ............................................... A61F 5/04
[52] U.S. Cl. ................................. 128/92 R; 128/92 A
[58] Field of Search ................. 128/92 R, 92 A, 92 G

[56] References Cited

FOREIGN PATENT DOCUMENTS

| 438413 | 1/1975 | U.S.S.R. | 128/92 R |
| 596231 | 2/1978 | U.S.S.R. | 128/92 R |
| 594974 | 4/1978 | U.S.S.R. | 128/92 A |
| 644471 | 1/1979 | U.S.S.R. | 128/92 A |
| 829108 | 5/1981 | U.S.S.R. | 128/92 A |
| 856449 | 8/1981 | U.S.S.R. | 128/92 R |

OTHER PUBLICATIONS

J. Biomed. Engng., 1980, vol. 2, Oct., pp. 265–271, Ma et al., "Tibial Lengthening Apparatus with Distractive Force Measurement System".
Acta Orthopedica Belgica, Tome 42, Suppl. 1, 1976, "Method Objective d'Appreciation des Deformations du Complexe os–Implant (In Vivo) Par Telemesure", by Sommelet et al.
Originalarbeiten, Helv. Chir. Acta 41, 455–457, 1974, "In Vivo Messung der Belastungsabhangangigen Knochendehnung", by Brennwald et al.
Quatrieme Symposium de Biomecanique Osseuse, CIBO, 21 Mai 1976, "Problemes Posés par l'utilisation des Jauges de Contraintes (In Vivo)", by R. Bourgois et al.

Primary Examiner—Robert P. Swiatek
Assistant Examiner—C. W. Shedd
Attorney, Agent, or Firm—Sughrue, Mion, Zinn, Macpeak and Seas

[57] ABSTRACT

The stability of an orthopedic assembly characterized by external fixation means in the form of a fixation bar provided with five assemblies of strain gauges having at least one gauge each, involves the measuring the amount of torsion of the bar by one of the assemblies and measuring of two perpendicular components of the amount of bending of the bar at two points of the bar via the remaining two pairs of assemblies and determining by means of the strain gauges of the amount of torsion and the amount of bending at the level of the clamps which connect the fixation bar to the pins and by the comparison of the determined levels of the torsion and bending with those capable of causing sliding of the clamps, the extent of stability of the orthopedic assembly.

2 Claims, 3 Drawing Figures

METHOD FOR DETERMINING THE STABILITY OF AN ORTHOPEDIC DEVICE COMPOSED OF AN EXTERNAL FIXATION BAR DURING SETTING OF BONE FRACTURES

FIELD OF THE INVENTION

The invention relates to a method for determining the stability of an orthopedic device during the setting of fractures composed of an external fixation bar provided with strain gauges for measuring stresses in the external system.

BACKGROUND OF THE INVENTION

External fixation systems used in bone surgery are intended to maintain the interfragmentary setting during the consolidation phase of the fracture or the osteotomy. These systems provide a mechanical connection with osseous levers and the outside medium. This orthopedic device comprises one or several fixation bars connected to at least two pins by means of clamps, said pins being fixed by known means to the bone fragments in the case of a fracture.

At present, the means principally used in medicine to evaluate the consolidation of a fracture are radiography and manual evaluation of the rigidity. Other methods, such as histological examination, study by isotopical marking, vibratory methods and the use of electric voltages of the bone have not passed the experimental stage. However, none of these methods at present enable direct measurement of the evolution of the mechanical resistance of the bone, nor do they the determine the mechanical stability of the osteosynthesis assemblies during stresses or revalidation movements. It is also known to evaluate the reconsolidation by means of external fixation bars fitted with a single ohmic strain gauge. However, the use of a single gauge renders the method dependent upon the skill of the surgeon to direct this gauge in accordance with a maximal deformation plane as only one component of bending is determined. This technique only enables relative measurements of the evolution of the reconsolidation of the fracture.

On the other hand it has appeared that the rehabilitation of patients is slowed by the fear of causing a new fracture due to an overload exceeding the callus and fixation resistances, and simultaneously causing irreversible sliding in the clamps and movement of the bone fragments in the fracture site.

The object of the present invention is the objective determination of the torsion and of the bending of the external fixation bar at the level of the two closest clamps, situated on the bar, on either side of the gauged part.

It is thus possible to evaluate the risk of sliding in these clamps by comparing the determined stresses to the stresses capable of being borne by these clamps.

SUMMARY OF THE INVENTION

The present invention relates to a method for determining the stability of an orthopedic device carried out by means of an external fixation, characterized by the use of a fixation bar provided with five assemblies of strain gauges having at least one gauge each, an assembly measuring the torsion of the bar and two pairs of assemblies measuring two perpendicular components of bending of the bar at two points of said bar, by the determination by means of these strain gauges of the torsion and of the bending at the level of the clamps which connect the fixation bar to the pins and by the comparison of the determined levels of torsion and of bending with those capable of causing sliding in the clamps.

The orthopedic assembly created by means of the external fixation can include one or several fixation bars. These bars may be of any type whatsoever. They are connected by at least two pins to the bone fragments. The assembly of bars may comprise interconnections.

The term "clamp" is used to mean any mechanical device connecting the various fixation elements to each other.

The term "strain gauge" is used to mean any device of a known type used for the measurement of mechanical strain. It includes, for example, any device whose electrical resistance varies as a function of its extension and thus enables the determination of the extension of an element with which it would be connected.

The five assemblies of strain gauges having at least one gauge each are necessary and sufficient to measure the stress in sliding of the clamps. It is not excluded to use supplementary assemblies fulfilling other functions, for example to measure the strains in traction-compression.

The claimed device determines by means of the first assembly the torsion value, which is constant up to the two closest clamps situated on either side of the point of measurement, and by means of two other pairs of assemblies, the bending along the bar and therefore at the level of these clamps, due to the knowledge at two points of its linear evolution.

In accordance with a preferred embodiment of the claimed method, each assembly of strain gauges comprises from one to four gauges. Since the measurements are normally carried out by Wheatstone bridges, each of which comprises four branches, it is not efficient to use more than four gauges per assembly. However, it is not excluded to use more than four gauges per assembly. In the case of use of an assembly comprising one single strain gauge for the measurement of the torsion, corrections must be made in order to take into account that the torsion gauge is also submitted to large bending stresses. The measurement of the deformations at the level of the gauges is obtained by connecting the strain gauges to any measuring apparatus of a known type, such as the strain indicator, fitted with a switch enabling rapid measurement of several groups of gauges. For example, the DMD 20 strain indicator and the UMK 10 switch from Hottinger Baldwin Messtechnik may be used for static measurements and the automatic switching and measurement installation UPH 3200 of Hottinger Baldwin Messtechnik may be used for dynamic measurements.

The determination of the torsion and bending at the level of the two closest clamps, situated on the bar on either side of the gauged part, is carried out by calculation on the base of the measurements described above. Since the torsion is constant along a straight bar, between two clamping points, the stress calculated at the level of the gauges can be directly compared to the limit value causing the sliding of the bar in the two closest clamps situated on the bar on either side of the point of measurement.

Since the bending and its components evolve in a linear manner along a straight bar, between two clamping points, it is necessary to know the distances between the points of measurement and the closest clamps situated on either side of the points of measurement. In this manner the value of the bending component at the level of these clamps can be extrapolated, the bending can be recomposed and the values obtained can be compared to the limit values causing the sliding of the clamps.

The stress limits of the clamps are values which are determined statistically, for a given type of clamp, by tests for example on a tensile strength machine.

In accordance with the present invention, the determination of the torsion and of the bending at the level of the clamps, and the comparison of their value with values capable of causing sliding in the clamps are carried out continuously by means of an apparatus for measuring and interpreting the results by logical program.

The invention will be more easily understood from the following non-limitative example. The bar, equipped with five assemblies of two gauges each is connected to a first small housing. This housing contains the high precision resistance necessary for the completion of the five assemblies of strain gauges so as to constitute Wheatstone bridges. The electrical signals collected at the terminals of these bridges are amplified by high performance, low drift amplifiers, then transmitted to a second housing. Here, the five signals are converted one after the other into a digital code. The electronics of this housing comprises a switching device which consecutively scrutinizes each analogical electric signal and transmits it to a high dynamics analogical digital converter. A microprocessor provides the addressing logic and selection of channel logic, as well as the transitory stocking, the coding and the serialization of the information. At the output of this housing, the digital information is transmitted to a processing center, either by cable, or by hertzian waves, or by any other means of transmission. The processing device is a microcomputer which has the necessary logic for decoding the information and calculating the value of the torsion and of bending. These values are compared to the limit values causing sliding in the clamps. This comparison is carried out progressively as the information is acquired. The method for determination of the stability of an orthopedic assembly in accordance with the present invention may comprise visual device or sound devices warning the operator in case of exceeding the imposed stress limits.

It is possible, in the embodiment described above, to program the microcomputer to control a cathode screen display, or to set off a sound signal via a relay when a limit considered reasonable by the user is exceeded.

In accordance with the claimed method, the fixation bar provided with five assemblies of strain gauges also enables the evolution of the consolidation of the fracture to be followed over a period of time.

During reference stresses of the total osteosynthesis bone-material assembly, the part of the stresses taken up by the bar itself is measured.

By repeating these measurements, as a function of the post-operative days, the decrease of the stresses taken up by the osteosynthesis bar can be followed, said decrease being correlated to the increase of callus rigidity. The apparatus can be provided with programs enabling the establishment, as a function of the post-operative days, of diagrams of evolution of the stresses taken up by the bar during reference stresses, for example bending of the hip in the laid position for fractures of the tibia. These diagrams are compared to pre-established curves so as to show the distinctions in relation to normal evolution.

The apparatus may possibly be provided with a printer, so as to provide a document summarizing the measurements taken.

The method, as claimed, will be more easily understood by means of the following drawings which in no case limit the invention.

DESCRIPTION OF PREFERRED EMBODIMENTS

Figure 1:
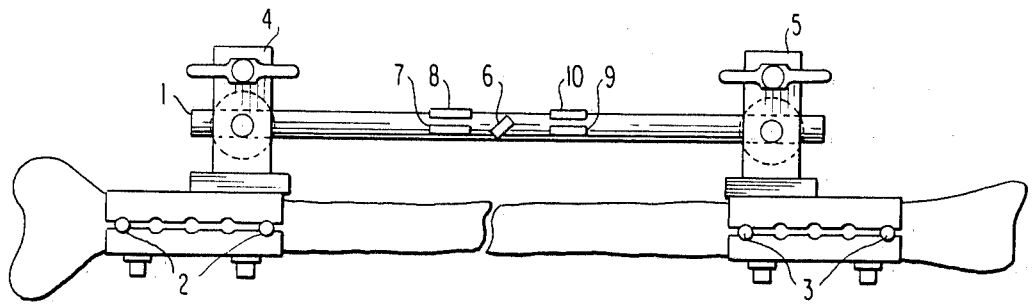
FIG. 1 is a plan view of a round fixation bar fitted with five assemblies of strain gauges each comprising one gauge.

In accordance with FIG. 1, the orthopedic assembly comprises a round fixation bar 1, connected, by means of clamps 4 and 5, to groups of pins 2 and 3, each composed of two pins. The fixation bar 1 is provided with five assemblies of one gauge each. Strain gauge 6 is arranged at 45° in relation to the generators and measures the torsion.

Gauges 7 and 8 form an assembly pair of one gauge each, and are arranged in accordance with two generators offset by 90° in a same straight cross-section. They provide the value of the bending components at this point.

Gauges 9 and 10 form a second assembly pair of one gauge each and are arranged in accordance with the same generators as gauges 7 and 8, respectively, but in a straight cross-section offset by a determined and known distance. They provide the value of the same bending components at this second point.

Figure 2:
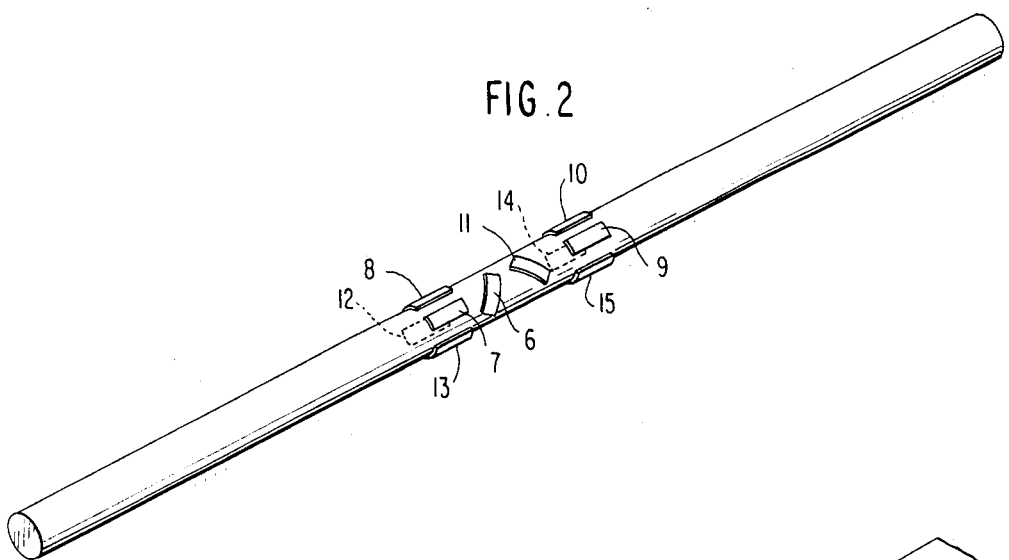
FIG. 2 is a perspective view of a round fixation bar fitted with five assemblies of strain gauges each comprising two gauges.

In FIG. 2, only the fixation bar is shown. It is connected to the bone fragments by means of pins and clamps, in the same way as is shown in FIG. 1.

Gauges 6 and 11, which constitute the assembly for the measurement of the torsion value, are arranged on a same generator and form an angle of 90° with each other and angles of 45° with the generators.

Gauges 7 and 12 and 8 and 13, respectively, are arranged in two perpendicular longitudinal sections of the bar and form two pairs of assemblies in a same transversal cross-section, measuring the value of the bending components at this point on the bar.

Gauges 9 and 14 and 10 and 15, respectively, are arranged in like manner, but in a transversal cross-section offset by a well-determined and known distance. They measure the value of the same bending components at this second point on the bar.

Figure 3:
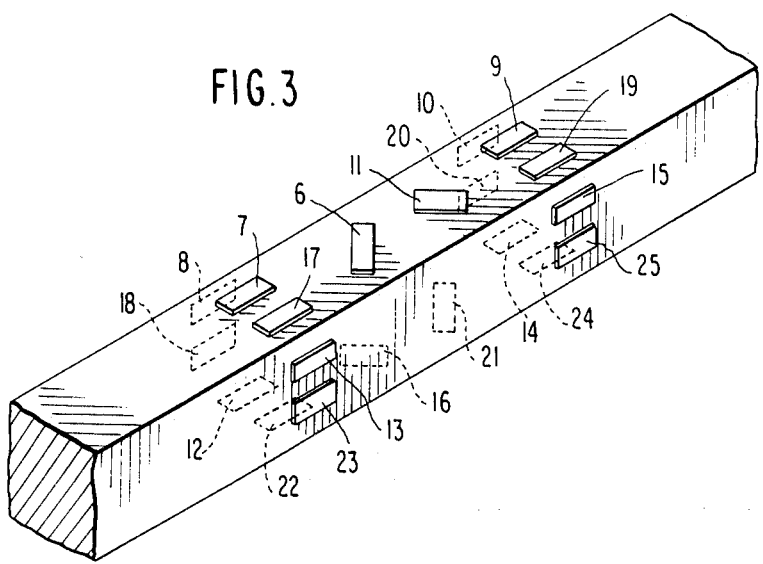
FIG. 3 is a perspective view of a square fixation bar fitted with five assemblies of strain gauges each comprising four gauges.

In accordance with FIG. 3, only the part of the bar containing the gauges is shown. The bar is fixed to the bone fragments in like manner to FIG. 1, and comprises assemblies of 4 gauges. The assembly for measurement of the torsion value is composed of gauges 6, 11, 16 and 21.

The pair of assemblies measuring the value of the bending components at a first point is composed, respectively, of gauges 7, 12, 17 and 22 and of gauges 8, 13, 18 and 23. The gauges are situated symmetrically in relation to two perpendicular longitudinal planes and in a same cross-section.

Gauges 9, 14, 19 and 24 and 10, 15, 20 and 25, respectively, constitute a second pair of assemblies measuring the value of the same bending components at a second point. They are situated in like manner to the gauges of the first pair of assemblies, but in a transversal cross-section offset by a well-determined and known distance.

In accordance with a preferred embodiment of the claimed method, the determination of the torsion and bending values, at the level of the clamps, from the signals emanating from the assemblies of gauges, and the comparison of these values capable of causing sliding in the clamps, is carried out continuously by means of apparatus for measuring and interpreting the results by logical processing.

One embodiment consists of using a microcomputer (not shown) fitted with the necessary electronic accessories for the amplificaton and digital conversion of the signals emanating from the gauges.

This microcomputer is provided with the program necessary for carrying out a rapid sampling of the signals from the gauges, calculating the torsion and bending value at the level of the clamps, and comparing, at each sampling, these values with values capable of causing sliding in the clamps, by taking into account a security factor determined by the operator before the measuring session.

What is claimed is:

1. A method for determining the stability of an orthopedic assembly produced by means of an external fixation, characterized by the use of a fixation bar connected by clamps to pins within bone fragments provided with five assemblies of strain gauges having at least one gauge each; said method comprising the steps of measuring the torsion of the bar via one of said five assemblies, measuring two perpendicular components of the bending of the bar at two points of said bar via the remaining two pairs of said assemblies, and determining by means of said strain gauges the amount of the torsion and the amount of the bending at the level of the clamps which connect the fixation bar to the pins, and by the comparison of the determined levels of torsion and bending with those capable of causing sliding in the clamps, determining the extent of stability of said orthopedic assembly.

2. The method for determining the stability of an orthopedic assembly produced by means of an external fixation, in accordance with claim 1, wherein said measurements comprise taking measurements from five assemblies of strain gauges comprising each from one to four gauges.

* * * * *